United States Patent [19]

Miya

[11] 4,252,689
[45] Feb. 24, 1981

[54] METHOD OF PRODUCING COPPER-IRON-ALUMINUM CATALYSTS

[75] Inventor: Bunji Miya, Wakayama, Japan

[73] Assignee: Kao Soap Co., Ltd., Tokyo, Japan

[21] Appl. No.: 52,420

[22] Filed: Jun. 27, 1979

[30] Foreign Application Priority Data

Jul. 3, 1978 [JP] Japan ................................ 53/80663

[51] Int. Cl.³ ........................ B01J 21/04; B01J 23/72; B01J 23/74
[52] U.S. Cl. ............................................... 252/466 J
[58] Field of Search .................................. 252/466 J

[56] References Cited

U.S. PATENT DOCUMENTS

| | | | |
|---|---|---|---|
| 2,449,295 | 9/1948 | Gutzeit | 252/466 J |
| 2,844,633 | 7/1958 | Braconier et al. | 568/885 |
| 3,197,418 | 7/1965 | Maebashi et al. | 568/885 |
| 4,144,198 | 3/1979 | Miya et al. | 252/466 J |

Primary Examiner—W. J. Shine
Attorney, Agent, or Firm—Blanchard, Flynn, Thiel, Boutell & Tanis

[57] ABSTRACT

A copper-iron-aluminum hydrogenation catalyst is prepared by separately and simultaneously adding dropwise to a bath of water (a) an aqueous solution of cupric, ferrous and aluminum salts and (b) an aqueous solution of alkali metal compound effective to precipitate the copper, iron and aluminum ions, and then agitating the reaction mixture at a temperature of at least 50° C., at a pH of 9.5 to 11.5, for from 10 minutes to 10 hours, then recovering the precipitate and treating it to convert it to an active catalyst.

5 Claims, No Drawings

METHOD OF PRODUCING COPPER-IRON-ALUMINUM CATALYSTS

The present invention relates to a method of producing copper-iron-aluminum catalysts for use in hydrogenation.

Straight-chain, higher alcohols are usually produced from fatty acid methyl esters by reduction with high pressure hydrogen at elevated temperatures. A copper-chromium oxide catalyst, generally called copper chromite catalyst, is used in the reaction. A method for the preparation of the catalyst is described in Industrial and Engineering Chemistry Vol. 26, pp. 878 (1936), but the method has made little progress up to the present. The method comprises adding ammonia to a dichromic acid salt dissolved in water, further adding a cupric salt to the resulting solution, filtering off the precipitate thereby produced, and subjecting the precipitate to washing with water, drying and calcining. This method has a serious drawback in that copper ions and large quantities of chromium (VI) ions are discharged in the filtration and water-washing processes because of the incomplete reaction between the reactants. These heavy metals are collected by an adequate method for the sake of prevention of environmental pollution. However, the final process for the disposal of the heavy metal sludge thereby produced has not yet been established. The inventor of this invention found a solution to the problem by use of a copper-iron-aluminum catalyst, and at the same time found a method for the production of the catalyst superior to the copper chromite catalyst in terms of performance, and completed the present invention.

That is, the present invention provides a method of producing copper-iron-aluminum catalysts which comprises simultaneously dropping an aqueous mixture (a) of a cupric salt, a ferrous salt and an aluminum salt and an aqueous alkali solution (b) containing an alkali amounting to the equivalent weight or more of the metals in the said aqueous mixture at room temperature or 50° C. or above in an reactor, agitating the resulting mixture at a temperature of 50° C. or above for 10 min. to 10 hr. after completion of dropping, subsequently separating, washing with water, drying and burning the precipitate thereby produced.

The inventor of this invention has already obtained with others, U.S. Pat. No. 4,144,198 concerning a method for the production of copper-iron-aluminum catalysts which comprises dissolving a cupric salt, a ferrous salt and an aluminum salt in water, subsequently adding an alkali at a temperature of 60° C. or above to form a precipitate, separating the precipitate, and subjecting the precipitate thus separated to washing with water, drying, calcining and grinding. The copper-iron-aluminum catalysts obtained according to the method described in the said patent application were superior to the copper chromite catalyst in terms of selectivity, life, etc., but the activity of the former was approximately similar to that of the latter. The present invention provides a method of producing copper-iron-aluminum catalysts having activities much superior to those of the catalysts obtained according to the method described in the above mentioned patent.

The present invention is characterized by the simultaneous dropping of an aqueous mixture of copper, iron and aluminum salts and an aqueous alkali solution. Many procedures are considered for the order of addition of the four types of reactants. They include, for example, a method which comprises adding an aqueous alkali solution to an aluminum salt, followed by dropping an aqueous mixture of copper and iron salts thereinto; a method which comprises dropping an aqueous alkali solution into an aqueous mixture of copper and iron salts, followed by dropping an aqueous aluminum salt solution thereinto; and a method which comprises dropping an aqueous mixture of copper, iron and aluminum salts into an aqueous alkali solution. Any of these methods gives good catalysts. However, it was found that the catalysts according to the method of this invention are best.

As described above, the method of this invention has a characteristic feature in that no heavy metals are discharged from the production process of the catalysts. Furthermore, the catalysts according to the method of this invention have the following features as compared to the copper chromite catalyst: (1) Much greater activity, (2) excellent selectivity, (3) excellent catalyst life, (4) small ignition properties after use, (5) No trouble occurs during plant operation because copper crystals do not deposit in a high pressure hydrogenation tower, and (6) inexpensive because inexpensive iron and aluminum salts are used in place of expensive dichromates.

The method of producing the catalysts by this invention will be described in detail below.

The cupric salt to be used in this invention includes, for example, cupric sulfate, cupric chloride, cupric nitrate, but cupric sulfate is best in terms of price. Also, ferrous sulfate, ferrous chloride, ferrous nitrate, etc. may be used as the ferrous salt, but ferrous sulfate is most suitable. Aluminum sulfate, aluminum chloride, aluminum nitrate and various types of alum may be used as the aluminum salt, but aluminum sulfate is most suitable. The quantitative ratio of iron and aluminum atoms each to a copper atom in the aqueous mixture of copper, iron and aluminum salts of this invention should preferably be 0.4–2.5, and 0.4–2.0, respectively. If the ratio deviates from the above ranges, the catalyst obtained has small activity, and at the same time forms many by-products when used in hydrogenation. Production of higher alcohols by hydrogenation of fatty acid methyl esters gives by-products such as hydrocarbons, ethers and secondary alcohols having an even and odd number of carbons.

In the method of this invention, lithium hydroxide, sodium hydroxide and potassium hydroxide may be used as the alkali required to form the precipitate, but sodium hydroxide is most suitable in terms of price. Ammonium hydroxide is inadequate because it produces a copper complex. The amount of alkali used should be over the amount required to precipitate all the copper, iron and aluminum ions as hydroxides. If this amount is taken as 100%, the amount of alkali used should preferably be 103% to 110%.

In the method of this invention the dropping of the aqueous mixture of copper, iron and aluminum salts may be carried out at room temperature or at an elevated temperature of 50° C. or more. If dropping is carried out at room temperature, it is necessary to elevate the temperature of the solution at 50° C. or above to dehydrate copper and iron hydroxides after completion of dropping. In either case, the solution is agitated for 10 min. to 10 hr. and preferably 30 min. to 3 hr. after completion of dropping. In order to produce a good catalyst, it is essential that the reaction liquid is adjusted always to pH 9.5–11.5 and preferably pH 10 to 11 during agitation with an acid or alkali. If the temperature is low or the pH value is low, dehydration of copper and iron hydroxides is not sufficiently carried out, yielding a poor catalyst. The amount of the aluminum salt lost as sodium aluminate is extremely small even at a high pH stated above. This indicates that the aluminum salt does not behave singly in the present reaction.

An X-ray diffraction pattern of the precipitate obtained at the end of the reaction shows peaks due to $Cu_2O$ alone, showing no peaks due to simple oxides and hydroxides of Cu, Fe and Al.

Filtration, centrifugal separation, settling, and other adequate processes may be used in separating the precipitate from the mother liquor after termination of the reaction. Various types of flocculants are effectively used in the separation processes. The precipitate separated is washed well with water to remove thoroughly water-soluble ions. Various types of flocculants are effectively used in a similar manner in the washing process. Next, the precipitate washed with water is dried by an adequate method, and the dried product is ground, if necessary. However, this treatment may be omitted.

The dried product is subsequently subjected to calcining at 550°–850° C. and preferable at 700°–800° C. A calcining temperature of 750° C. is most preferable. If treated at a temperature of 550° C. or less, the catalyst obtained has a great activity, but with poor selectivity. If treated at 850° C. or above, the activity unfavorably decreases, and the sintering of catalyst particles becomes marked. Calcining is adequately carried out for 0 min. to 2 hrs. after a desired calcining temperature is obtained. The calcined product is ground, if necessary, to yield a desired catalyst.

The X-ray diffraction pattern of a catalyst obtained according to the method of this invention shows peaks due to $Fe_3O_4$, but shows no peaks attributable to CuO, $Fe_2O_3$, $Al_2O_3$ and other simple substances. No peaks attributable to ferrite are present. The X-ray diffraction pattern of the catalyst used for high pressure hydrogenation shows peaks due to $Fe_3O_4$ alone, and no other peaks are present. The catalyst after use has strong magnetism.

The present invention is described in detail with reference of the following examples.

EXAMPLE 1

Zero point 409 mole of $CuSO_4.5H_2O$, 0.491 mole of $FeSO_4.7H_2O$ and 0.266 mole of $Al_2(SO_4)_3.18H_2O$ were added to 500 ml of water. The atomic ratio of Cu/Fe/Al was 1/1.2/1.3. Separately, 466 g of an aqueous 30% NaOH solution was prepared. The amount of NaOH is 103% of the theoretical value. A reaction flask containing 400 ml of water was maintained at 90° C., to which the said two solutions were simultaneously added dropwise in 30 min. The pH of the mixture at completion of dropping was 8.3. The pH was adjusted to 10.0 by use of an aqueous NaOH solution, and then the reaction was continued for 2 hr. at 90° C. The precipitate produced was separated by settling by use of a polyacrylamide flocculant, and was washed with water until the sulfate ion level decreased to 1 ppm (calculated value). The product washed with water was dried, calcined at 750° C. for 1 hr., and ground to yield a catalyst. No heavy metal ions were detected in the mother liquid separated from the precipitate.

Six g of the catalyst was added to 200 g of coconut oil fatty acid methyl ester, and the reaction was carried out at 275° C. and 150 $Kg/cm^2$ hydrogen pressure in a 500 ml autoclave. The hydrogen was discarded every 30 min. to remove methanol produced by the reaction, and was replaced by new hydrogen. Small amounts of samples were collected at 30, 90, 120, 150, 180 and 210 min. after starting the reaction, and were washed with water to determine their saponification values and the amount of by-products (hydrocarbons, ethers, secondary alcohols) by gas chromatography. From the saponification values at 30 and 90 min. ($S_1$, $S_2$), the first-order reaction rate constant K (1/hr.) was determined according to the following equation: $K=\ln[(S_1-8)/(S_2-8)]$, where 8 is the equilibrium saponification value at 275° C. and 150 $Kg/cm^2$. Zero-order reaction rate constant B (%/hr.) was determined from the amounts of by-products at, and after 120 min. K was 3.15 and B was 0.82. The same experiments were carried out with the copper chromite catalyst, and K and B were 1.51 and 0.56, respectively. That is, the K value for the catalyst of this example was 2.09 times greater the K value for the copper chromite catalyst. R, the ratio of B and K (R=B/K) represents a comparison of the rate of formation of by-products when the rate of the main reaction was controlled to be constant by adjusting the amount of catalyst. The value R for the catalyst of this example was 0.26, and that for the copper-chromite catalyst was 0.37, which indicated that the catalyst of this example has a good selectivity.

EXAMPLES 2-5

Catalysts were prepared in a manner similar to that in Example 1 except that the number of moles of $CuSO_4.5H_2O$, $FeSO_4.7H_2O$, $Al_2(SO_4)_3.18H_2O$ and the weight of the aqueous NaOH solution were variously changed and the pH of the mixture during agitation after dropping both solutions was adjusted to 10.5. Coconut oil fatty acid methyl ester was hydrogenated in the presence of the catalyst in a manner similar to that in Example 1. The results are shown in Table 1. For all the examples, their K and R values are favorably greater than those for the copper chromite catalyst.

TABLE 1

| | Example No. | | | |
|---|---|---|---|---|
| | 2 | 3 | 4 | 5 |
| $CuSO_4.5H_2O$ Mole | 0.500 | 0.346 | 0.409 | 0.409 |
| $FeSO_4.7H_2O$ Mole | 0.400 | 0.554 | 0.491 | 0.491 |
| $Al_2(SO_4)_3.18H_2O$ Mole | 0.325 | 0.225 | 0.348 | 0.184 |
| Cu/Fe/Al Atomic ratio | 1/0.8/1.3 | 1/1.6/1.3 | 1/1.2/1.7 | 1/1.2/0.9 |
| 30% NaOH Weight, g | 515 | 433 | 534 | 399 |
| K | 3.90 | 2.07 | 2.68 | 2.26 |
| B | 0.68 | 0.69 | 0.89 | 0.71 |
| R | 0.17 | 0.33 | 0.33 | 0.32 |

EXAMPLE 6

Seven point five g of the catalyst in Example 1 was used for the hydrogenation of coconut oil fatty acid methyl ester, and the catalyst was recovered for the catalyst life test as described next. The recovered catalyst was added to 150 g of coconut oil fatty acid methyl ester, and the reaction was carried out at 275° C. and 250 $Kg/cm^2$ hydrogen pressure for 3.5 hr. to observe the time required to reach a 90% conversion on the basis of the amount of hydrogen absorbed. The catalyst was separated from the reaction mixture at the completion of the reaction, and was supplied to the second reaction. This procedure was repeated several times. The specific activity was determined by dividing the time required to reach 90% conversion for the first reaction by that for each reaction. Similar experiments were carried out with the copper chromite catalyst, and the results shown in Table 2 were obtained. The value in the parenthesis is the time (min.) required to reach 90% conversion.

TABLE 2

| Number of uses | Specific activity | | | | | | |
|---|---|---|---|---|---|---|---|
| | 1 | 2 | 3 | 4 | 5 | 6 | 7 |
| Catalyst in Example 1 | 1.00 (27) | 1.04 (26) | 1.00 (27) | 0.87 (31) | 0.93 (29) | 0.82 (33) | 0.69 (39) |
| Copper chromite catalyst | 1.00 (49) | 1.04 (47) | 1.02 (48) | 0.82 (60) | 0.79 (62) | 0.71 (69) | 0.65 (75) |

The results revealed that the life of the catalyst in Example 1 is comparable or superior to the copper chromite catalyst.

EXAMPLE 7

The catalyst in Example 1 was subjected to a reaction. The catalyst after use was easily adhered to a magnet. The catalyst used was separated from the alcohol, and the catalyst containing 30% alcohol was heated. It ignited at 144° C. The same experiments were carried out with the copper chromite catalyst. Its ignition temperature was 127° C. According to the electron-microscopic photographs of the catalysts after use, no crystal deposition was noted for the catalyst in Example 1, but deposition of many copper crystals of some 10 microns was observed for the copper chromite catalyst.

EXAMPLE 8

To 200 g of furfural were added 0.8 g of $Ca(OH)_2$ and 0.5 g of the catalyst in Example 1, and the reaction was carried out at 160° C. and a hydrogen pressure of 120 $Kg/cm^2$ to produce furfuryl alcohol. The reaction completed in 20 min. The reaction products comprises 98.0% furfuryl alcohol and 0.2% unreacted furfural.

What is claimed is:

1. The method of preparing a copper-iron-aluminum catalyst, which consists essentially of the steps of:
   adding dropwise to a bath of water contained in a reaction vessel,
   (a) an aqueous solution of cupric salt, ferrous salt and aluminum salt, said solution (a) containing from 0.4 to 2.5 atoms of iron and from 0.4 to 2.0 atoms of aluminum per one atom of copper, and simultaneously adding dropwise to said bath of water, separately from said solution (a),
   (b) an aqueous solution of an alkali metal compound effective to precipitate all of the copper, iron and aluminum ions contained in said solution (a) as the corresponding hydroxides,
   then, after completion of said simultaneous steps of adding said solution (a) and said solution (b) to said bath of water to form a reaction mixture, agitating the reaction mixture for from 10 minutes to 10 hours, at a temperature of from 50° C. to a temperature lower than the boiling point of the reaction mixture and effective to dehydrate copper and iron hydroxides, while maintaining the reaction mixture at a pH of from 9.5 to 11.5, whereby to form a precipitate;
   then separating the precipitate from the reaction mixture, washing the precipitate with water, drying the precipitate and calcining the precipitate at a temperature of from 550° to 850° C. to obtain the copper-iron-aluminum catalyst.

2. The method as claimed in claim 1 in which said alkali metal compound is sodium hydroxide.

3. The method as claimed in claim 1 or claim 2 in which said cupric salt is cupric sulfate, said ferrous salt is ferrous sulfate and the aluminum salt is aluminum sulfate.

4. The method as claimed in claim 1 in which, in said agitating step, the reaction mixture is maintained at a pH of from 10 to 11, and in said calcining step the temperature is from 700° to 800° C.

5. The method as claimed in claim 1 in which the amount of said alkali metal compound added to said bath of water is from 1.03 to 1.1 of the amount required to precipitate all of the copper, iron and aluminum ions contained in said solution as the corresponding hydroxides.

* * * * *